United States Patent [19]

Singery et al.

[11] Patent Number: 4,692,154
[45] Date of Patent: Sep. 8, 1987

[54] CATHETER GUIDE

[75] Inventors: Denis C. Singery, Hoffman Estates; Ronald O. Gordon, Rolling Meadows, both of Ill.

[73] Assignee: Illinois Tool Works Inc., Chicago, Ill.

[21] Appl. No.: 869,416

[22] Filed: Jun. 2, 1986

[51] Int. Cl.⁴ ........................................... A61M 25/00
[52] U.S. Cl. .................................... 604/172; 604/271
[58] Field of Search ................................. 604/171–172, 604/271; 128/756

[56] References Cited

U.S. PATENT DOCUMENTS 3,421,509  1/1969  Fiore ................................... 604/171
4,324,262  4/1982  Hall .................................. 604/271 X

FOREIGN PATENT DOCUMENTS 2031733  4/1980  United Kingdom ................ 604/171

Primary Examiner—Dalton L. Truluck
Attorney, Agent, or Firm—David I. Roche; Thomas W. Buckman

[57] ABSTRACT

A catheter guide having a tubular body of a resilient material with flexible closure means located at the distal end of the tubular body which can be manipulated into various open and closed positions to permit introduction of lubricating material and to protect the catheter from bacteria within the body passage.

3 Claims, 11 Drawing Figures

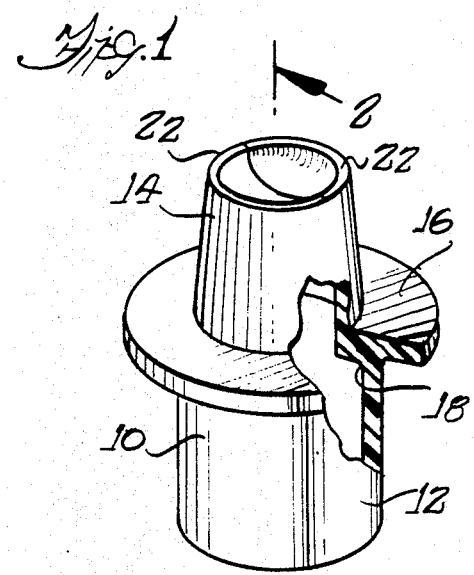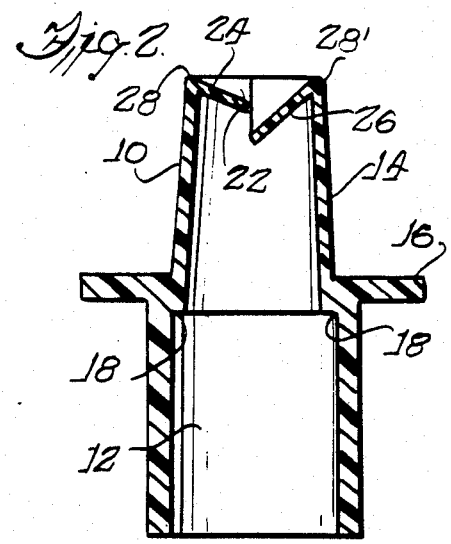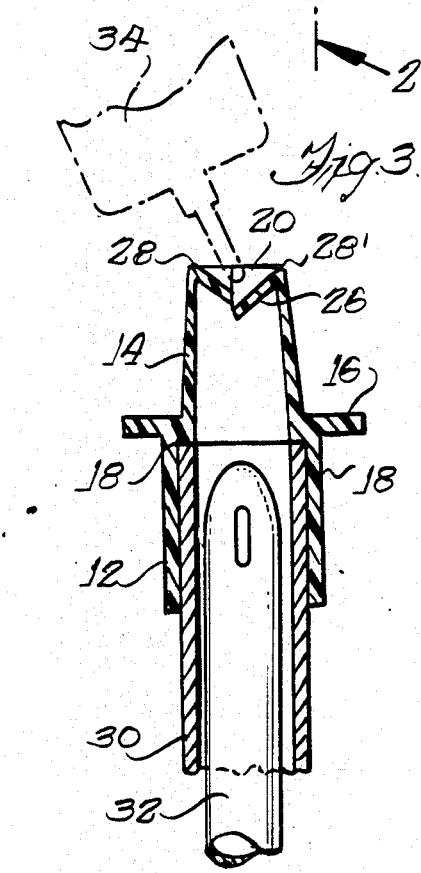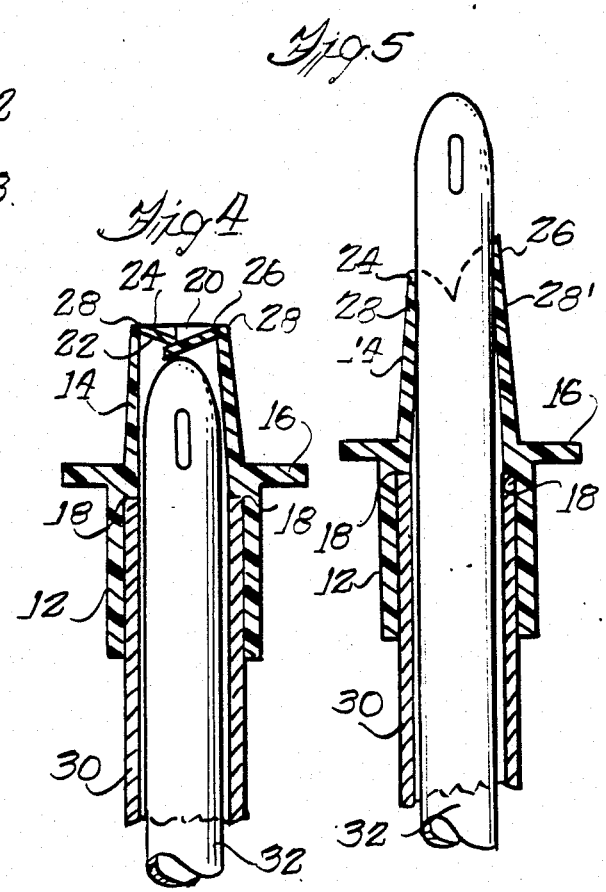

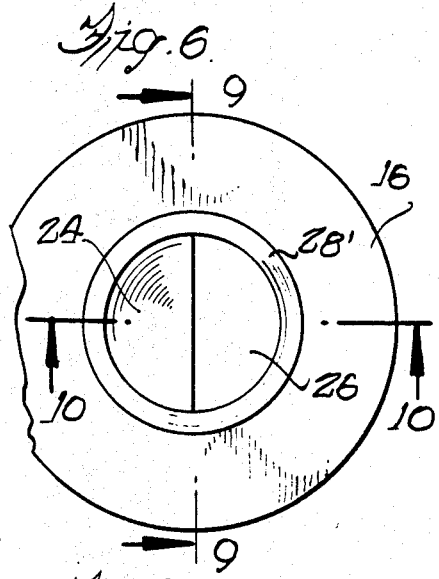
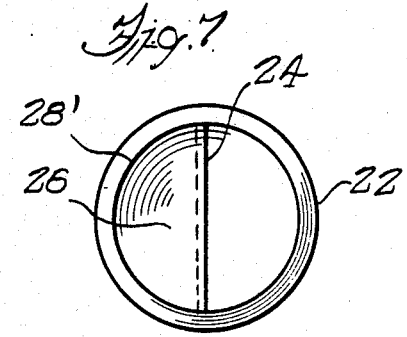
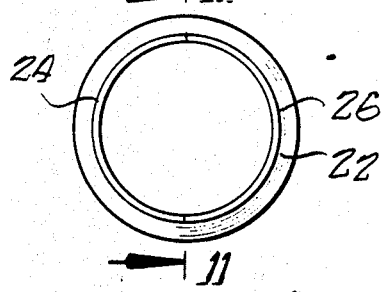
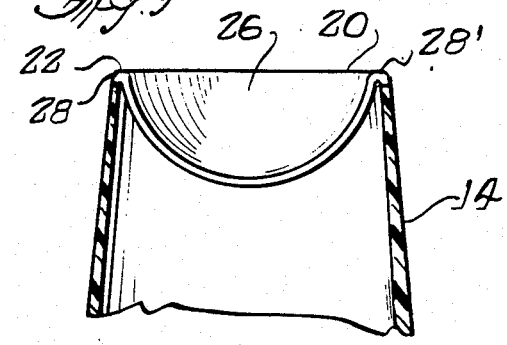
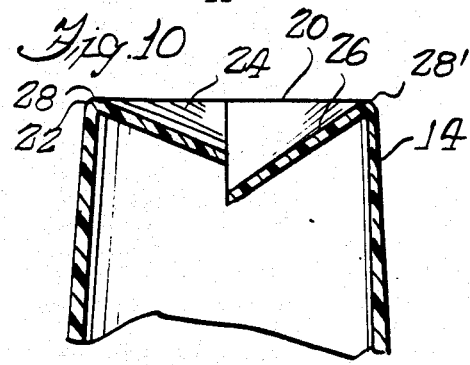
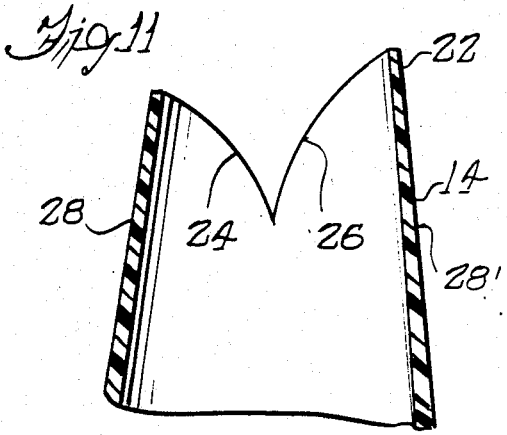

CATHETER GUIDE

BACKGROUND OF THE INVENTION

This invention relates to a catheter guide device and more particularly a catheter guide with novel closure means for use in inserting a catheter tube through a urethra into a bladder.

Urethral catheters are well-known medical instruments utilized to remove urine from the bladder for various medical purposes. A urethra catheter is a long, thin, flexible and sterile tubulation which is inserted into the urethra to progress past the trigone muscle and into the bladder to withdraw urine therefrom.

It is of extreme importance that the catheter is sterile as it enters the bladder to prevent the transmission of harmful bacteria to the patient from a contaminated instrument. The catheter can become contaminated by harmful bacteria that is present at the fossa navicularis or outer end of a urethra.

It is also desirable that the catheter is lubricated in such a way so that it can be pushed easily and comfortably through the urethra into the bladder.

In the past, it has been difficult if not impossible to prevent the catheter from being contaminated by the bacteria which are present at the fossa navicularis or outer end of a urethra when passing therethrough. It has also been difficult to sufficiently lubricate the catheter in such a way as to avoid contamination. If the catheter is lubricated before it is inserted into the catheter guide it can become contaminated in the process of lubrication.

Although, such prior art devices as shown in Canadian Pat. No. 1,152,837 have attempted to solve this problem, none have been totally successful.

Accordingly, it is an object of the present invention to provide an improved catheter guide having flexible closure means to allow lubrication of the catheter and to prevent contamination of the catheter.

It is a more specific object of this invention to provide a simple and economical one-piece catheter guide that is of a predetermined length in excess of the outer end of the urethra, with resilient flexible closure means.

It is a further object of this invention to provide said closure means capable of being manipulated in a first open position that allows the insertion of lubricating material for the catheter, and a second closed position as the catheter guide enters the outer end of the urethra and a third open position that allows the catheter to travel through the guide into the urethra to the bladder virtually free of contaminates.

BRIEF DESCRIPTION OF THE DRAWINGS

The features of the present invention which are believed to be novel are set forth with particularlity in the appended claims. The organization and manner of operation of the invention, together with further objects and advantages thereof, may best be understood by reference to the following description taken in connection with the accompanying drawings in the several figures of which like reference numerals identify like elements, and in which:

FIG. 1 is a partially broken away perspective view of the novel catheter guide;

FIG. 2 is a sectional view of the catheter guide taken along line 2—2 of FIG. 1;

FIG. 3 is a partial sectional view of the catheter guide, showing closure means thereof in an open position, for receiving lubricating material;

FIG. 4 is a partial sectional view of the catheter guide, showing closure means thereof in a closed position when the catheter is manually pushed to the distal end of the guide;

FIG. 5 is a partial sectional view of the catheter guide showing the closure means in an extended upright position when the catheter is manually pushed through the distal end of the guide, forcing the closure means to extend upward;

FIG. 6 is an end view of the catheter guide in the condition it is shown in FIG. 3;

FIG. 7 is an end view of the catheter guide in the condition as it is shown in FIG. 4;

FIG. 8 is an end view of the catheter guide in the condition as it is shown in FIG. 5;

FIG. 9 is an enlarged fragmentary sectional view taken along line 9—9 in FIG. 6;

FIG. 10 is an enlarged fragmentary sectional view taken along line 10—10 in FIG. 6; and FIG. 11 is an enlarged fragmentary view taken along line 11—11 in FIG. 8.

DETAILED DESCRIPTION OF THE ILLUSTRATED EMBODIMENT

Turning first to FIG. 1 there is shown, a novel catheter guide 10 embodying the present invention. The catheter guide 10 is preferably made of a flexible and resilient silicone rubber or other suitable material. The catheter guide 10 comprises a hollow tubular body 12 with a tapered nozzle portion 14. The nozzle 14 has a predetermined diameter that allows the nozzle portion 14 to be comfortably inserted into the urethra. The nozzle 14 also has a predetermined length, which is at least as long as the length of the outer end of the urethra which is where the harmful bacteria is located. The catheter guide 10 includes a flange or stop member 16. The stop member 16 extends outwardly from the bottom end of nozzle 14 for engaging an area around the entrance of the urethra on insertion of the guide 10 into the urethra thereby limiting the insertion of the guide 10 into the urethra. The catheter guide 10 includes an inner stop or ledge member 18 that extends inwardly from the bottom end of the nozzle 14. The guide 10 also comprises closure means 20 for sealing the distal end 22 of the nozzle portion 14.

Turning now to FIG. 2 the closure means 20 is comprised of a first flap means 24 of a predetermined length which extends inwardly from one side of the distal end 22 and a second flap means 26 of a predetermined length which extends inwardly from the opposite side of the distal end 22 and inclines inwardly to an initial position beneath the first flap means 24. The second flap 26 is longer than the first flap 24 to provide sealing interference or overlapping in the closed position.

As shown best in FIGS. 2, 3, 4 and 5 the first flap means 24 and the second flap means 26 are joined to the nozzle portion 14 along a juncture or hinge line 28 and 28' respectively. The width of the side walls of the nozzle portion 14 are gradually tapered from the lower end of the nozzle 14 toward the distal end 22 of the nozzle 14 which increases the flexibility of the hinge members 28 and 28' to allow said flap members 24 and 26 to be manipulated in various open and closed positions.

As illustrated best in FIGS. 3, 4 and 5 a rigid sheath member 30 fits into the tubular body 12 so that the top of the sheath member 30 lies adjacent to and is flush against the inner ledge member 18. During use, the sterile catheter 32 is placed inside rigid sheath member 30 which is used to guide the catheter into the tubular body 12. The rigid sheath or tube 30 is self supporting and may be used in the manner of a handle for manipulating the catheter while the guide 10 is of relatively soft, pliable and resilient material for facilitating entry of the nozzle portion 14 into the urethra. Preferably the body 12 has an internal diameter slightly less than the diameter of the tube 30 and is stretched thereover to provide for secure assembly between the sheath or tube 30 and the guide 10.

Turning now to FIGS. 3, 6 and 10 it is shown that the first flap means 24 and the second flap means 26 are in a first or open position so that a lubricating material 34 can be introduced into the catheter guide 10 through the closure means 20 at the distal end 22. This enables lubrication of the catheter 32 while it is inside the sterile catheter guide 10 so that it will not be contaminated by humans or the outside environment. It also enables the catheter to become sufficiently lubricated so it can pass through a urethra of a patient easily and comfortably.

Turning now to FIGS. 4, 7 and 9, when the catheter is to be applied to a patient, the catheter 32 is first manually pushed up into the nozzle 14 sufficiently so that the tip of the catheter 32 pushes the second flap means 26 to a second or closed position against the first flap 24 effectively sealing the distal end 22 of the catheter guide 10. Then the nozzle portion is inserted into the urethra while the distal end 22 remains closed so that bacteria in the outer end of the urethra cannot reach the catheter.

As shown in FIGS. 5, 8 and 11, as the catheter 32 is pushed past the lower end of the nozzle portion 14, the tip of the catheter pushes the closure means 20 to a third or open position. In other words, the flaps 24 and 26 are flexed along the hinges or junction lines 28 and 28' into an upright or an extended position. The extension of flap means 24 and flap means 26 serves to extend the length of the side walls of the nozzle 14 so that the catheter 32 is further shielded from harmful bacteria in the outer end of the urethra enabling the catheter 32 to enter the bladder free of contaminants.

While particular embodiments of the invention have been shown and described in detail, it will be obvious to those skilled in the art that changes and modifications of the present invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A catheter guide for use in inserting a catheter through a urethra into a bladder comprising a molded one-piece device of resilient material having a tubular portion of a predetermined length which is insertable partially into the urethra, and a plurality of flaps integral with the tubular portion and located at a distal end of said tubular portion, said flaps being molded in a first position, said flaps in said first position extending toward each other and away from said distal end into said tubular portion and said flaps having lengths such that an opening is formed for allowing lubricating material to be inserted into the guide through said opening after the catheter has been inserted partially into the tubular portion, said flaps being manipulatable by the catheter into a second closed position, the length of said flaps allowing said flaps to abut one another for preventing contamination of the catheter as said guide enters a urethra and said flaps being manipulatable by the catheter into a third position with said flaps extending out of said tubular portion for permitting the catheter to pass therethrough.

2. A catheter guide according to claim 1, wherein said flaps are reduced in thickness increasing the flexibility of said flaps as the catheter is manipulated through the guide as it enters a urethra.

3. A catheter guide according to claim 1, wherein said flaps are initially molded so that one flap is longer than another and the longer flap lies beneath and is spaced from the other flap so that the lubricating material can be inserted into the distal end of the guide.

* * * * *